United States Patent [19]

Ingber et al.

[11] Patent Number: 5,674,073
[45] Date of Patent: Oct. 7, 1997

[54] IMPRESSION COPING

[75] Inventors: Abraham Ingber, Potomac; Vincent Joseph Prestipino, North Bethesda, both of Md.

[73] Assignee: Nobel Biocare AB, Gothenburg, Sweden

[21] Appl. No.: 594,302

[22] Filed: Jan. 30, 1996

[51] Int. Cl.⁶ .................................................. A61C 11/00
[52] U.S. Cl. ............................................. 433/213; 433/173
[58] Field of Search .................................. 433/213, 214, 433/173

[56] References Cited

U.S. PATENT DOCUMENTS

| | | | |
|---|---|---|---|
| 4,708,654 | 11/1987 | Branemark | 433/173 |
| 4,955,811 | 9/1990 | Lazzara et al. | 433/213 |
| 5,125,841 | 6/1992 | Carlsson et al. | 433/172 |
| 5,213,502 | 5/1993 | Daftary | 433/214 |
| 5,334,024 | 8/1994 | Niznick | 433/173 |
| 5,538,426 | 7/1996 | Harding et al. | 433/214 |

OTHER PUBLICATIONS

Knode, Rehabilitation With Implant–Supported Suprastructures At The Time Of The Abutment Surgery: A Case Report, The Cosmetic Dentistry Edition 1995, pp. 67–73.

*Primary Examiner*—Cary E. O'Connor
*Attorney, Agent, or Firm*—Pollock, Vande Sande & Priddy

[57] ABSTRACT

An impression coping for transferring the inclination and position of a dental implant fixture or abutment to a working model has a base portion which provides for rotational locking to a fixture head or an abutment and an elongated upper part projecting from the base portion to provide for retention in a surrounding impression mold. The entire impression coping is made of an elastic material so that a clamp fitting is obtained between the base portion and the fixture head or abutment. The base portion comprises a downwardly projecting, unthreaded guide pin adapted for insertion into the internal bore in the fixture head or abutment during installation of the impression coping, thereby facilitating the centering and positioning of the coping during placement.

8 Claims, 1 Drawing Sheet

IMPRESSION COPING

FIELD OF THE INVENTION

The present invention relates to an impression coping for transferring the direction and position of a dental implant fixture or abutment to a working model.

BACKGROUND OF THE INVENTION

Impression copings are used by dental professionals for making positive cast models for the manufacture of dentures and specifically dental prostheses of the type which are permanently anchored in the jaw by means of one or more securing elements, i.e. "fixtures," implanted in the jawbone. The fixtures are placed endosteally using special instruments, and the procedure is designed to cause a minimum of trauma to the living bone tissue, Normally there is a second surgical procedure in which the mucosa is opened again and an abutment of a length which corresponds to the thickness of the gingiva is connected to the fixture. The part of the abutment which protrudes above the gingiva constitutes the distance between the base of the permanent prosthesis and the underlying mucosa.

Dental prostheses which are anchored in this way on abutments must be carefully adapted to the actual appearance of the jaw. In most cases, when treating totally edentulous jaws by using osseointegrated fixtures, the topography of the mucosa is of less importance, It is, on the other hand, very important to get an extremely accurate idea of the position of the abutments in relation to one another. The permanent prosthesis must fit exactly in order to avoid internal design stress and prevent accompanying complications.

In those instances in which abutments are mounted on osseointegrated implants, the taking of impressions requires somewhat different procedures than is the case with complete denture therapy. Thanks to the technique of lifting out special transfer copings enclosed in the impression material, extremely high accuracy is obtained in the relation of the abutments to one another on the model.

The technique for taking impressions is known and will not be described in any detail here. Reference is made, for instance, to U.S. Pat. No. 4,708,654 which describes how a positive working model of a lower or upper jaw provided with protruding abutments can be produced.

The production of the positive working model is facilitated with the aid of the components included in the impression system, namely impression copings, guide pins and abutment replicas.

The impression copings are used for transfer of the intraoral fixture position to the plaster model. They are attached to the abutments with the guide pins which have a lower screw thread and an upper slot for a tool. The length of the guide pins is determined by the amount of space available. An impression tray is then tried out over the copings and the impression material is applied intraorally around the copings.

After a predetermined setting time, the guide pins are loosened from the abutments and the impression is lifted out from the mouth. The abutment replicas are then screwed onto the pins which have remained in the impression material, the impression is disinfected and then sent to the dental laboratory.

There are two standard types of impression copings, namely squared impression copings which are used for most indications, specifically with more rigid impression materials, like plaster or polyether material, and tapered impression copings which are used only with resilient impression material, such as class A silicones or polyether material. The tapered impression copings are most commonly used in cases of partial edentulism where there is not enough room to take an impression using squared copings.

The squared copings are attached to the abutments by means of guide pins, as already mentioned, while tapered copings have an integral screw so that the coping can be attached by that screw to the abutment and tightened by hand.

These copings are preferably made of titanium and the abutment replicas are made of stainless steel.

To facilitate the abutment connection, specifically to make it easier for the dentist to choose an appropriate abutment for the individual situation, there is an advantage if this selection of abutment type or size can be effectuated outside the mouth on a model. Therefore it is also previously known to take an impression on the fixture level, in which case, the impression coping fits directly onto the fixture head. This requires a slightly different impression coping having a base which fits the fixture head and, instead of an abutment replica, a fixture replica is used.

This type of coping also has markings for abutment height selection. It is used with a special guide pin with a lower screw thread for attaching the coping to the internal screw hole in the fixture head.

All of these prior art impression copings that now have been discussed are attached to the metallic (titanium) abutment, or specifically in case of single-tooth restoration, to the titanium fixture itself a screw and they are therefore made of metal, preferably titanium. They can be used in cases where the abutment or the fixture comprises an internal thread in which the guide pin can be screwed down. However, other types of abutments which do not have an internal screw thread are also on the market. Particularly in single-tooth restorations, a type of abutment is also used whose base portion, as in previous abutments, is adapted to the upper part of the fixture but having an upper, elongated narrower part of hexagonal design. There is no internal screw thread in this abutment and the conventional type of impression coping with separate guide pins for screw connection cannot be used.

An impression coping adapted for this type of single-tooth restoration system is described in U.S. Pat. No. 5,125,841. This impression coping, or impression top, is made of an elastic material so that a clamp fitting is obtained between the base part of the device and the abutment, which means a connection which should be completely free from play. The impression coping has a base portion with an internal hexagonal recess which permits rotational locking against the abutment. Also, it has an upper part whose geometry provides for retention in the surrounding impression compound, and it is provided with break notches so that it can easily be shortened. In this case also, the abutment replica, which is used as an analogue in the working cast during the laboratory procedure, is made of plastic. Generally, this type of impression coping can also be used for impression taking on the fixture level, but the base portion of the coping illustrated in the above-identified patent is not adapted to a standard fixture head.

To provide a more customized formation and fitting of a dental prostheses, it is also known to make the entire abutment of a ceramic material such as aluminum oxide so that it may be readily surface bonded to various superstructure materials, see U.S. Pat. No. 5,125,839. This facilitates a customized formation of a dental implant assembly such as is outlined in the patent. Different standard sized prefabricated abutments made of an aluminum oxide ceramic material are available for selection of an abutment (post) to meet individual requirements of dental patients who have implantation of titanium fixtures. The selected post can be cut to a desired axial length and then attached to the bone-embedded fixture.

Of course, impression taking is necessary also in connection with this type of ceramic abutment and an impression coping would be required. There are specific demands on a ceramic abutment system from an aesthetical point of view, however, which means that the previous impression copings are not fully efficient and satisfying. Specifically, the aforementioned plastic impression coping does not give an optimal fitting if used directly on the fixture head, because it is difficult to recognize a distinct and correct position onto the fixture head as the protruding hex is comparatively low.

Furthermore, when used on the abutment level, there might be no problem in positioning the coping properly since the abutment protrudes well above the gingiva, but when used directly on the fixture head, it is more difficult as the upper level of the fixture head is normally located below the gingiva.

It should also be pointed out that there are some new methods for the surgical operation in which the impression is carried out by means of a resin template pattern (See article, "Rehabilitation With Implant-Supported Suprastructures At The Time Of The Abutment Surgery: A Case Report" by Dr. Helmuth Knode) in which the intraoral fixture position is transferred to a model as soon as the fixture has been installed, i.e. before the healing phase. This is an attractive method as the individual abutment procedure can be finished much earlier. In this case, however, there is a risk that the transverse rods 6 on the elongate beam 5 of the prior plastic impression coping described in U.S. Pat. No. 5,125,841 could harm the surrounding soft tissue when the coping is installed.

SUMMARY OF THE INVENTION

It is an object of this invention to provide an impression coping of the aforementioned type made of an elastic material which facilitates proper connection of the coping to an abutment or fixture head during the impression taking procedure.

It is a further object of this invention to provide an impression coping with reduced risk for harming or disturbing the surrounding tissue when used in situations where the available space is limited.

According to the present invention, an impression coping for transferring the inclination and position of a dental implant fixture or abutment to a working model comprises a base portion which provides for rotational locking against the fixture or abutment and an elongated upper part projecting from the base portion and with a geometry that provides for retention in a surrounding impression compound. The coping is made of an elastic material so that a clamp fitting is obtained between its base portion and the fixture or abutment. The base portion comprises an unthreaded, integral guide pin projecting downwardly from the bottom end of the base portion in the longitudinal direction of the elongated upper part of the impression coping.

The integral guide pin is to be inserted into the upper bore of the abutment or fixture.

In a preferred embodiment, the elongated uppermost part is provided with retention means in the form of annular grooves.

BRIEF DESCRIPTION OF THE DRAWINGS

One embodiment of the present invention will be described in detail with respect to the accompanying drawings in which.

DETAILED DESCRIPTION OF THE PREFERRED EMBODIMENT

Figure 4:
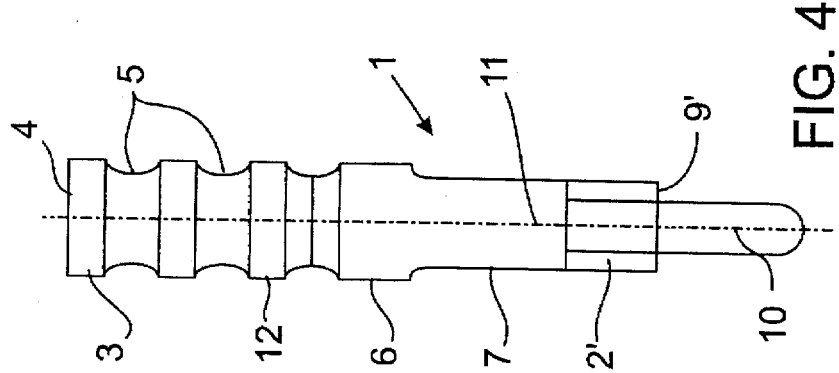
FIG. 4 is an alternative embodiment of the impression coping of the present invention.
Figure 2:
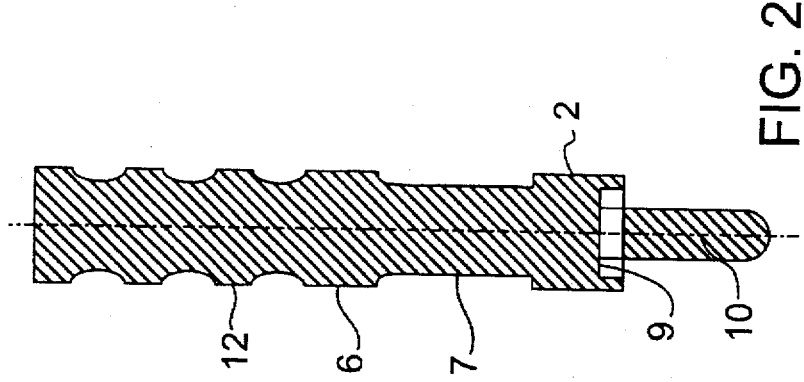
FIG. 2 is a cross-sectional view of the impression coping shown in FIG. 1.
Figure 1:
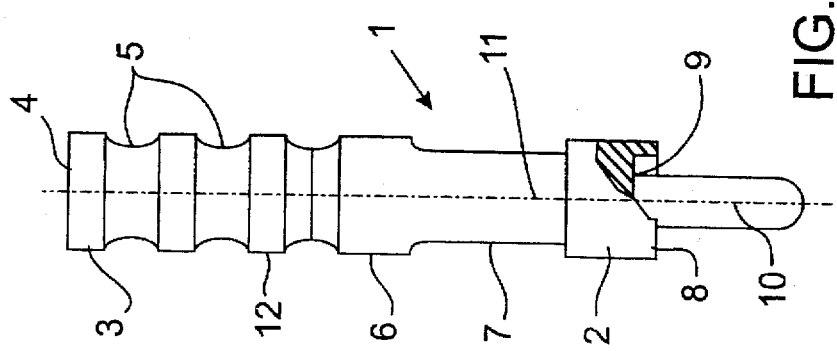
FIG. 1 is a side view of an impression coping in accordance with the present invention.

The impression coping is made as a generally cylindrical elongated member 1 comprising a base portion 2 and an upper part 3 with a geometry that provides for retention in the surrounding impression compound. The upper part has a planar end surface 4 and the cylindrical surface has a number of annular retention grooves 5 on the uppermost part, a cylindrical mid-section 6 and a lower reduced diameter section 7.

The circular end surface 8 of the base portion 2 has an internal hexagonal recess 9 which accurately receives the protruding hexagon of the fixture head (not shown). The hexagonal recess 9 has a protruding central pin 10 extending from the end surface of the base portion 2 in the longitudinal direction 11 of the coping. The pin 10 has a length which is less than the length of the internal bore in the head of the fixture, and it has a diameter which is less than the internal screw thread diameter. The pin 10 facilitates the positioning, specifically the centering, of the coping on the fixture head as the pin goes into the internal bore. The pin maintains the coping in a central position with respect to the fixture during placement. The pin is made as an integral part of the body of the impression coping. The entire impression coping is made of an elastic material, for example plastic, so that a clamp or press fitting is obtained between the base portion 2 and the fixture head, which means a connection completely free from play.

In contrast to previous impression copings, the elongated upper part has a comparatively long, reduced diameter bottom section without any retention means. This reduces the risk of interference with the surrounding tissue when the available space is limited for the placement of the impression coping. Furthermore the retention means on the uppermost part are in the form of annular grooves instead of transverse rods like the impression coping illustrated in the above-mentioned U.S. Pat. No. 5,125,841. Also, the mid-section has an extension which is approximately at least twice the length of the bulbs 12 between the annular grooves. This mid-section facilitates the gripping of the coping during insertion.

Figure 3:
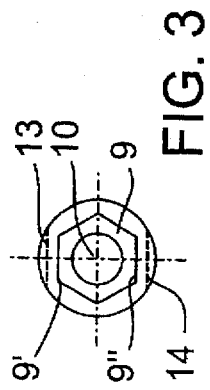
FIG. 3 is a bottom view of the impression coping shown in FIG. 1.

As illustrated in FIG. 3, the coping has a circular cross-section. However, the circular surface might be provided with two diametrically opposed flat surfaces as indicated by dashed lines 13, 14 in the figure. The flat surfaces 13, 14 are "keyed" to the hexagonal surfaces in the recess 9, i.e. they are parallel to the surfaces 9' and 9" in the recess. These flat surfaces provide a certain resistance to rotational movement in the impression material, and they also provide an indication to the user of the orientation of the hex, i.e. the rotational indexing means.

The invention is not limited to the embodiment described here but can be varied within the scope of the accompanying claims. Specifically, it should be understood that the impression coping could be connected to an abutment instead of the fixture head when such impression taking is desired, as long as the abutment also is provided with a central internal bore to match the protruding guiding pin on the base portion of the coping.

Even if a circular cross-section might be preferred, it should also be understood that, for instance, a rectangular cross-section of the body 1 might be useful.

FIG. 4 illustrates an alternative embodiment of the impression coping to be used with fixtures having an internal hexagonal recess (polygonal recess) on the head portion thereof. In this case, the base portion 2' of the impression coping has an external hexagonal (polygonal) configuration 9' which accurately fits into the internal hexagonal recess of the fixture head. As in the first embodiment, the hexagonal base portion of the impression coping has a protruding central pin 10 extending from the end surface of the base portion which goes into the internal bore of the fixture head.

In this disclosure, there are shown and described only the preferred embodiments of the invention, but, as aforementioned, it is to be understood that the invention is capable of use in various other combinations and environments and is capable of changes or modifications within the scope of the inventive concept as expressed therein.

We claim:

1. An impression coping for transferring the inclination and position of a dental implant fixture or abutment to a working model, said impression coping comprising a base portion which provides for rotational locking against the fixture or abutment and an elongated upper part projecting from said base portion and having a geometry that provides for retention in a surrounding impression compound, the coping being made of an elastic material so that a clamp fitting is obtained between its base portion and the fixture or abutment;

said base portion comprising an unthreaded, integral guide pin projecting downwardly from the bottom end of the base portion in the longitudinal direction of the elongated upper part of the impression coping.

2. An impression coping according to claim 1 wherein said pin has a dimension adapted to the dimension of an inner bore of a fixture head or the abutment so that the pin easily goes into said bore during installation of the impression coping onto the fixture head or the abutment thereby facilitating the positioning of the coping during placement.

3. An impression coping according to claim 2 wherein the elongated upper part comprises an uppermost section with retention means, a cylindrical mid-section, and a lower reduced diameter section.

4. An impression coping according to claim 3 wherein said uppermost section comprises retention means in the form of annular grooves.

5. An impression coping according to claim 1 wherein said base portion has an internal polygonal recess which corresponds with accurate fitting to the protruding polygonal configuration of a fixture head.

6. An impression coping according to claim 1 further having a substantially cylindrical outer surface with rotational indexing means in the form of longitudinally extending flat surfaces.

7. An impression coping according to claim 6 wherein the rotational indexing means are keyed to the surfaces of an internal polygonal recess.

8. An impression coping according to claim 1 wherein said base portion has an external polygonal configuration which corresponds with accurate fitting to an internal polygonal recess of a fixture head.

* * * * *